(12) United States Patent
Meleqi et al.

(10) Patent No.: US 12,426,826 B2
(45) Date of Patent: Sep. 30, 2025

(54) METHOD FOR CHARACTERIZING AN OLFACTORY STIMULATION

(71) Applicants: ROBERTET S.A., Grasse (FR); Université Côte d'Azur, Nice (FR); CENTRE NATIONAL DE LA RECHERCHE SCIENTIFIQUE, Paris (FR)

(72) Inventors: Xhino Meleqi, Cannes (FR); Anthony Pegard, Grasse (FR); Jérémie Topin, Nice (FR)

(73) Assignees: ROBERTET S.A., Grasse (FR); UNIVERSITÉ CÔTE D'AZUR, Nice (FR); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 405 days.

(21) Appl. No.: 17/989,309

(22) Filed: Nov. 17, 2022

(65) Prior Publication Data

US 2023/0148941 A1    May 18, 2023

(30) Foreign Application Priority Data

Nov. 17, 2021   (FR) ..................... 21/12153

(51) Int. Cl.
    *A61B 5/00*    (2006.01)
(52) U.S. Cl.
    CPC ............ *A61B 5/4011* (2013.01); *A61B 5/742* (2013.01)
(58) Field of Classification Search
    CPC ......... A61B 5/4011; A61B 5/742; A61B 5/72; A61B 5/7271
    See application file for complete search history.

(56) References Cited

U.S. PATENT DOCUMENTS

| 7,955,259 B2 * | 6/2011 | Lee ....................... A61M 21/00 600/27 |
| 2007/0066916 A1 | 3/2007 | Lemos |

(Continued)

FOREIGN PATENT DOCUMENTS

WO    2019220428 A1    11/2019

OTHER PUBLICATIONS

Written Opinion for FR Application No. 21/12153; 5 pages.

*Primary Examiner* — Eric F Winakur
(74) *Attorney, Agent, or Firm* — CANTOR COLBURN LLP

(57) ABSTRACT

A method for characterizing an olfactory stimulation, including visual stimulation steps each associated with a theme and first steps of recording physiological variables carried out continuously during a first visual stimulation step, so as to obtain first physiological recordings, each first physiological recording being associated with the theme associated with the first visual stimulation step, a second olfactory stimulation step, a second step of recording values of physiological variables carried out continuously during and after the second olfactory stimulation step to obtain a second physiological recording, a step of comparing the first physiological recordings with the second physiological recording to isolate a first physiological recording close to the second physiological recording, and a step of determining a theme associated with the first physiological recording which is isolated during the comparing step.

20 Claims, 1 Drawing Sheet

(56) References Cited

U.S. PATENT DOCUMENTS

| | | | |
|---|---|---|---|
| 2008/0255949 A1 | 10/2008 | Genco et al. | |
| 2012/0220857 A1 | 8/2012 | Warr | |
| 2014/0303450 A1 | 10/2014 | Caponi | |
| 2021/0256542 A1* | 8/2021 | Mcdaniel | A61B 5/4011 |
| 2021/0406983 A1* | 12/2021 | Lee | A61B 5/0533 |

* cited by examiner

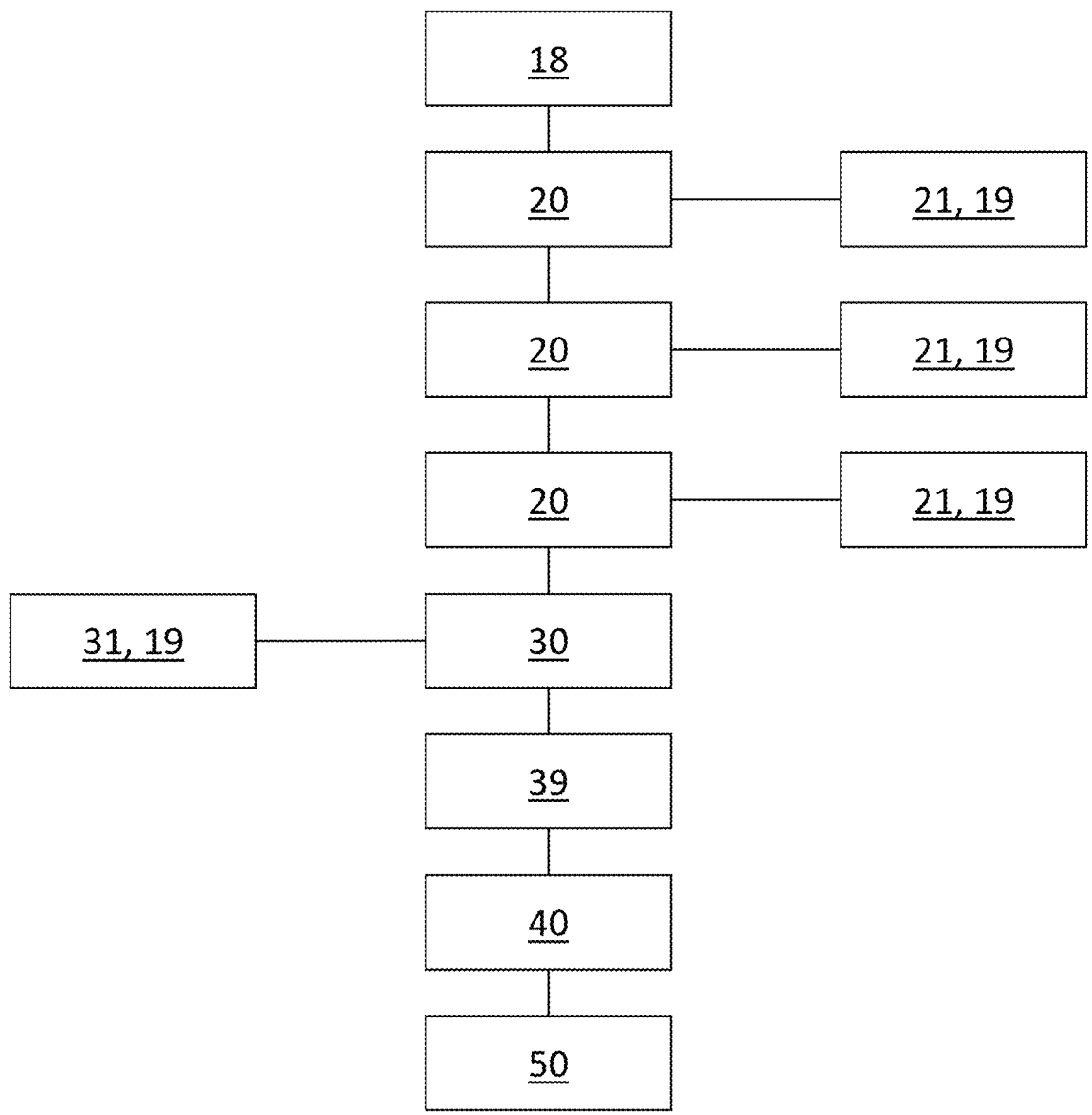

METHOD FOR CHARACTERIZING AN OLFACTORY STIMULATION

CROSS REFERENCE TO RELATED APPLICATIONS

This application claims priority under 35 U.S.C. § 119 to the following French Patent Application No. FR 21/12153, filed on Nov. 17, 2021, the entire contents of which are incorporated herein by reference thereto.

FIELD OF THE INVENTION

The present invention relates to a method for characterizing an olfactory stimulation, and more particularly to the characterization of an olfactory stimulation using an identified theme.

PRIOR ART

In a known manner, the document US20120220857A1 concerns a method for detecting the release of dopamine following an olfactory stimulation. It is thus possible to characterize fragrances based on the release, or not, of dopamine.

However, these solutions are not completely satisfactory.

Indeed, the characterization presented in the document US20120220857A1 allows characterizing the fragrances only based on the release of dopamine, which therefore represents only two categories, the fragrances which release dopamine and those which do not.

The present invention aims to solve all or part of the abovementioned drawbacks.

DISCLOSURE OF THE INVENTION

To this end, the present invention concerns a method for characterizing an olfactory stimulation, the method comprising:
  a plurality of first visual stimulation steps, each first visual stimulation step consisting in carrying out a visual stimulation, each visual stimulation being associated with at least one identified theme;
  a plurality of first steps of recording values of physiological variables, each first recording step being carried out continuously during a first visual stimulation step among the plurality of first visual stimulation steps, so as to obtain a first physiological recording, the plurality of steps of recording values of physiological variables thus resulting in obtaining a plurality of first physiological recordings, each first physiological recording being associated with an identified theme corresponding to the identified theme associated with the first visual stimulation step;
  a second olfactory stimulation step, the second olfactory stimulation step consisting in carrying out an olfactory stimulation;
  a second step of recording values of physiological variables, the second step of recording values of physiological variables being carried out continuously during and after the second olfactory stimulation step thus resulting in obtaining a second physiological recording;
  a comparing step, the comparing step consisting in comparing the first physiological recordings with the second physiological recording, so as to isolate at least one first physiological recording, said at least one first isolated physiological recording being close to the second physiological recording; and
  a determining step, the determining step consisting in determining at least one identified theme, the identified theme being the identified theme associated with the at least one first visual stimulation step which is isolated during the comparing step.

In the context of the present invention, a plurality of first visual stimulation steps, each first visual stimulation step consisting in carrying out a visual stimulation, each visual stimulation being associated with at least one identified theme is a plurality of first stimulation steps, each first stimulation step consisting in carrying out a visual stimulation, each visual stimulation being associated with at least one identified theme.

In the context of the present invention, a second olfactory stimulation step, the second olfactory stimulation step consisting in carrying out an olfactory stimulation is a second stimulation step, the second stimulation step consisting in carrying out an olfactory stimulation.

In the context of the present invention, an identified theme can be of all kinds such as a type of emotion or even a cinematographic genre for example.

According to one embodiment, the visual stimulation step is a step in which a video is shown to a user. Such an arrangement allows for a better visual stimulation.

According to one embodiment, the video is a virtual reality video. Such an arrangement allows for a better immersion and therefore a better visual stimulation.

According to one embodiment, each visual stimulation lasts for thirty seconds. Such an arrangement allows carrying out the steps of recording values of physiological variables with better accuracy. This allows, for example, carrying out the calculation of the heart rate variability at high frequencies as well as at low frequencies. In the context of the present invention, the low frequencies are comprised between 0.04 Hz and 0.15 Hz inclusive. In the context of the present invention, the high frequencies are greater than 0.15 Hz and smaller than 0.4 Hz inclusive.

According to one embodiment, the identified theme is a theme identified by at least one user. In other words, it is a set of users comprising at least one user who chooses which identified theme is associated with each visual stimulation. And is therefore specific to each user. Such an arrangement allows for a good characterization of an olfactory stimulation. According to a preferred embodiment, the identified theme is identified by at least 50% of the users to be considered valid. According to one embodiment, during the second olfactory stimulation step, the sense of sight is restricted. Such an arrangement allows limiting disturbances such as natural visual stimulations and thus obtaining a better olfactory stimulation.

According to one embodiment, the second olfactory stimulation step consists in moving an element which produces a sensation of smell substantially four centimeters closer to the user's nose. Such an arrangement allows for a good olfactory stimulation. In the context of the present invention, substantially four centimeters means between three and a half centimeters and four and a half centimeters.

According to a preferred embodiment, the second olfactory stimulation step consists in moving an element which produces a sensation of smell closer to a user's upper lip.

According to one embodiment, the element is contained in a bottle or on a blotter. In the context of the present invention, a blotter can be of all kinds, so that said blotter can be soaked with a liquid, such as a paper or a sponge for example.

The second recording step being carried out continuously during and after the second olfactory stimulation step so as to obtain a second physiological recording, this allows comparing a first part of the second physiological recording which is recorded during the second olfactory stimulation step with a second part of the second physiological recording in order to more accurately characterize said olfactory stimulation.

According to one embodiment, the determining step is carried out using any method such as an ascending hierarchical classification and/or using a principal component analysis and/or using the dynamic clustering method for example.

The physiological variables can be of all kinds such as:
the heart rate in the high and low frequencies in order to determine the balance between the sympathetic and parasympathetic nervous system;
the galvanic skin response, in order to reveal an awakening state or a stress state for example; and
the respiratory rhythm in order to reveal a physiological state and to confirm the states deduced by the other physiological variables or derivatives.

According to one embodiment, the method comprises a first step of recording reference measurements, the first step of recording reference measurements being carried out before any one of the stimulation steps and consisting in continuously measuring values of physiological variables in order to obtain a first reference recording.

According to one embodiment, the method comprises a second step of recording reference measurements, the second step of recording reference measurements being carried out after or during any one of the stimulation steps and consisting in continuously measuring values of physiological variables in order to obtain a second reference recording.

According to one embodiment, the physiological recordings comprise recordings made using a photoplethysmogram placed on a distal phalanx of a middle finger, and preferably on a distal phalanx of a middle finger of a non-dominant hand of a user. Such an arrangement allows obtaining an accurate measurement. A photoplethysmogram placed on the distal phalanx of the middle finger of the non-dominant hand allows facilitating any manipulation that the user would have to perform. Indeed, said user would then be able to use a dominant hand.

According to one embodiment, the physiological recordings comprise recordings made with a photoplethysmogram placed on a distal phalanx of a thumb, and preferably of the non-dominant hand of the user. Such an arrangement allows obtaining an accurate measurement when the distal phalanx of the middle finger is too small. A photoplethysmogram placed on the distal phalanx of the thumb of the non-dominant hand allows facilitating any manipulation that the user would have to perform. Indeed, said user would then be able to use a dominant hand.

According to one embodiment, the physiological recordings comprise recordings made using two electrodermal conductance electrodes on the medial phalanxes of index and ring fingers, and preferably of the non-dominant hand of the user. Such an arrangement allows obtaining an accurate measurement. Placing the electrodermal conductance electrodes on the medial phalanxes of the index and ring fingers allows facilitating any manipulation that the user would have to perform. Indeed, said user would then be able to use a dominant hand.

According to one embodiment, the physiological recordings comprise recordings made using a skin temperature sensor on a distal phalanx of a little finger, and preferably of the non-dominant hand of the user. Such an arrangement allows obtaining an accurate measurement. A temperature sensor placed on the distal phalanx of a middle finger of the non-dominant hand allows facilitating any manipulation that the user would have to perform. Indeed, said user would then be able to use a dominant hand.

According to one embodiment, an averaging of the skin temperature for each of the two parts of each physiological recording is performed.

According to one embodiment, the physiological recordings comprise recordings of the respiratory volumes.

Such an arrangement allows deducing the respiratory rhythm.

According to one embodiment, the recordings of the respiratory volumes comprise the respiratory rhythm as well as the inspiration and expiration volumes.

Such an arrangement allows accurately deducing the physiological state of the user. In other words, this allows deducing whether the user is, for example, in a relaxed state or an agitated state.

According to one embodiment, the recordings of the respiratory volumes are made using an abdominal belt allowing measuring a thoracic or abdominal expansion and contraction of the user and thus generating a respiration wave corresponding to the variations of a respiratory volume.

Such an arrangement allows obtaining recordings of more accurate respiratory volumes.

According to one embodiment, the abdominal belt is located at the sternum. Such an arrangement allows obtaining recordings of more accurate respiratory volumes.

According to one embodiment, each first visual stimulation step comprises a first rest sub-step carried out after the visual stimulation, the first rest sub-step consisting in no longer carrying out stimulation for a first predefined time.

According to one embodiment, the first predefined time is calculated based on the respiratory rate of the user and corresponds to a first number of predefined cycles. Such an arrangement allows obtaining an accurate method for characterizing an olfactory stimulation, regardless of the respiratory rate of the user.

According to one embodiment, the second step of recording reference measurements is carried out during a rest sub-step. Such an arrangement allows obtaining a second more reliable reference recording.

According to one embodiment, the first predefined time is forty seconds. Such an arrangement allows carrying out a first visual stimulation step lasting thirty seconds and giving the user ten seconds to calm down and/or express any discomfort.

According to one embodiment, each second olfactory stimulation step comprises a second rest sub-step carried out after the olfactory stimulation, the second rest sub-step consisting in no longer carrying out stimulation for a second predefined time.

Such an arrangement allows giving the user the second predefined time to calm down and/or express any discomfort.

According to one embodiment, the second predefined time is thirty seconds. Such an arrangement allows obtaining a longer second step of recording values of physiological variables, which allows performing some calculations using the values of physiological variables with greater accuracy. It is, for example, possible to more accurately calculate the heart rate variability of the user.

According to one embodiment, the physiological recordings are divided and filtered.

According to one embodiment, the physiological recordings are divided in phases, each phase corresponding to one or several steps of the method. According to a preferred embodiment, there is a first phase corresponding to the plurality of first visual stimulation steps as well as to the plurality of first steps of recording values of physiological variables, and a second phase corresponding to the second olfactory stimulation step as well as to the second step of recording values of physiological variables.

According to one embodiment, the physiological recordings can be filtered of all kinds, such as by "smoothing" or artefact correction functions for example. Such an arrangement allows obtaining better quality physiological recordings.

According to one embodiment, a heart rate variability is calculated in the frequency and time domain.

According to one embodiment, a heart rate variability is calculated in the frequency domain using a Fourier transform from the time between the heart beats. A power calculation in the frequency domain is then performed. Such an arrangement allows highlighting some characteristics of the physiological recordings and thus obtaining a more accurate olfactory stimulation characterization.

According to one embodiment, the phasic and tonic skin conductances are calculated and represent the measurement of the electrodermal reaction.

Such an arrangement allows, based on the measurement of the electrodermal reaction, deducing the activity of the sympathetic nervous system.

In the context of the present invention, the term skin conductance means the galvanic skin response.

According to one embodiment, a reference statistical analysis step is carried out by comparing averages of physiological recordings originating from different steps of recording values of physiological variables.

Such an arrangement allows highlighting the different perceptions between the stimulations and thus grouping together the characterized stimulations.

According to one embodiment, the method for characterizing an olfactory stimulation also comprises a statistical analysis step carried out between the stimulations. The statistical analysis step is performed by normalizing the variations between before and after the stimulation. The normalization can be carried out of all kinds such as according to the following formula:

$$Vn = \frac{X - Y}{Y}$$

With:

Vn: normalized variation of any one of the physiological variables or any one of its derivatives;

X: a value of any one of the physiological variables or any one of its derivatives after a stimulation; and Y: a value of any one of the physiological variables or any one of its derivatives before a stimulation.

A statistical study is carried out for each of the physiological variables and each of its derivatives in order to compare the different stimulations.

According to one embodiment, the statistical study comprises the use of a statistical method such as the variance analysis.

According to one embodiment, the statistical study comprises the use of a statistical test such as the Student test.

The different non-incompatible aspects defined above can be combined.

BRIEF DESCRIPTION OF THE FIGURES

The invention will be even better understood from the detailed description that is set out hereinbelow with reference to the appended drawing in which:

FIG. 1 represents a sequence diagram of a method for characterizing an olfactory simulation in accordance with the present invention.

DESCRIPTION WITH REFERENCE TO THE FIGURES

FIG. 1 represents the steps of the method for characterizing an olfactory stimulation. Said method comprising a plurality of first visual stimulation steps 20, each first visual stimulation step 20 consisting in carrying out a visual stimulation by showing a video to a user. Such an arrangement allows fora better visual stimulation. According to a preferred embodiment, the video is a virtual reality video, such an arrangement allows for a better immersion and therefore a better visual stimulation.

Each visual stimulation is associated with at least one identified theme. The identified theme can be of all kinds such as a type of emotion or even a cinematographic genre for example. The identified theme is a theme identified by the user. In other words, it is the user who chooses which identified theme is associated with each visual stimulation. And is therefore specific to each user. Such an arrangement allows for a good characterization of an olfactory stimulation.

Each first visual stimulation step 20 comprises a first rest sub-step carried out after the visual stimulation, the first rest sub-step consisting in no longer carrying out stimulation for a first predefined time. The first predefined time is calculated based on the respiratory rate of the user and corresponds to a first number of predefined cycles. Such an arrangement allows obtaining an accurate method for characterizing an olfactory stimulation, regardless of the respiratory rate of the user. Advantageously, the first predefined time is forty seconds. Such an arrangement allows carrying out a first visual stimulation step 20 lasting thirty seconds and giving the user ten seconds to get used to virtual reality.

The method comprises a plurality of first steps of recording values of physiological variables 21, each first recording step being carried out continuously during a first visual stimulation step 20 among the plurality of first visual stimulation steps, so as to obtain a first physiological recording, the plurality of steps of recording values of physiological variables thus resulting in obtaining a plurality of first physiological recordings, each first physiological recording being associated with an identified theme corresponding to the identified theme associated with the first visual stimulation step 20.

Each visual stimulation lasts for thirty seconds. Such an arrangement allows carrying out the steps of recording values of physiological variables with better accuracy. This allows, for example, calculating the heart rate variability at high frequencies as well as at low frequencies. In the context of the present invention, the low frequencies are comprised between 0.04 Hz and 0.15 Hz inclusive. In the context of the present invention, the high frequencies are greater than 0.15 Hz and smaller than 0.4 Hz inclusive.

The method also comprises a second olfactory stimulation step 30, the second olfactory stimulation step 30 consisting in carrying out an olfactory stimulation. The second olfactory stimulation step consists in moving an element, which produces a sensation of smell, four centimeters close to the user's nose. Such an arrangement allows for a good olfactory stimulation. Said element is contained in a bottle or on a blotter. In the context of the present invention, a blotter can be of all kinds, so that said blotter can be soaked with a liquid, such as a paper or a sponge for example. During the second olfactory stimulation step 30, the sense of sight is restricted. Such an arrangement allows limiting disturbances such as natural visual stimulations and thus obtaining a better olfactory stimulation.

A second step of recording values of physiological variables 31 is then carried out. The second step of recording values of physiological variables 31 is carried out continuously during and after the second olfactory stimulation step 30 thus resulting in obtaining a second physiological recording. The second recording step is carried out continuously during and after the second olfactory stimulation step 30, so as to obtain a second physiological recording, this allows comparing a first part of the second physiological recording which is recorded during the second olfactory stimulation step 30 with a second part of the second physiological recording in order to more accurately characterize said olfactory stimulation.

Each second olfactory stimulation step 30 comprises a second rest sub-step carried out after the olfactory stimulation, the second rest sub-step consisting in no longer carrying out stimulation for a second predefined time. Such an arrangement allows obtaining a longer second step of recording values of physiological variables 31, which allows performing some calculations using the values of physiological variables with greater accuracy. It is, for example, possible to more accurately calculate the heart rate variability of the user. According to one embodiment, the second predefined time is thirty seconds. Such an arrangement allows obtaining a longer second step of recording values of physiological variables 31, which allows performing some calculations using the values of physiological variables with greater accuracy. It is, for example, possible to more accurately calculate the heart rate variability of the user.

The physiological variables can be of all kinds such as:
the heart rate in high and low frequencies in order to determine the balance between the sympathetic and parasympathetic nervous system;
the galvanic skin response, in order to reveal an awakening state or a stress state for example; and
the respiratory rhythm in order to reveal a physiological state and to confirm the states deduced by the other physiological variables or derivatives.

The physiological recordings comprise recordings made using a photoplethysmogram placed on a distal phalanx of a middle finger and/or on a distal phalanx of a thumb. Such an arrangement allows obtaining an accurate measurement when the distal phalanx of the middle finger is too small.

The physiological recordings comprise recordings made using two electrodermal conductance electrodes on the medial phalanxes of the index and ring fingers. Such an arrangement allows obtaining an accurate measurement.

The physiological recordings comprise recordings made using a skin temperature sensor on the distal phalanx of the little finger. Such an arrangement allows obtaining an accurate measurement. An averaging of the skin temperature for each of the two parts of each physiological recording is also carried out.

The physiological recordings comprise recordings of respiratory volumes. Such an arrangement allows deducing the respiratory rhythm. 1. The recordings of the respiratory volumes comprise the respiratory rhythm as well as the inspiration and expiration volumes. Such an arrangement allows accurately deducing the physiological state of the user. In other words, this allows deducing whether the user is, for example, in a relaxed state or an agitated state. The recordings of the respiratory volumes are made using an abdominal belt allowing measuring a thoracic or abdominal expansion and contraction and thus generating a respiration wave corresponding to the variations of a respiratory volume. Such an arrangement allows obtaining more accurate recordings of respiratory volumes. Preferably, the abdominal belt is located at the user's sternum, and more specifically so that a measuring case of the abdominal belt is located at the user's sternum. Such an arrangement allows obtaining more accurate recordings of respiratory volumes.

The physiological recordings are then divided and filtered in phases, each phase corresponding to one or more steps of the method. Advantageously, there is a first phase corresponding to the plurality of first visual stimulation steps 20 as well as to the plurality of first steps of recording values of physiological variables 21, and a second phase corresponding to the second olfactory stimulation step 30 as well as to the second step of recording values of physiological variables 31. The physiological recordings are filtered of all kinds such as by "smoothing" or artefact correction functions for example. Such an arrangement allows obtaining better quality physiological recordings.

A heart rate variability is calculated in the frequency and time domain using a Fourier transform from the time between the heart beats. A power calculation in the frequency domain is then performed. Such an arrangement allows highlighting some characteristics of the physiological recordings and thus obtaining a more accurate olfactory stimulation characterization.

The phasic and tonic skin conductances are calculated and represent the measurement of the electrodermal reaction. Such an arrangement allows, based on the measurement of the electrodermal reaction, deducing the activity of the sympathetic nervous system. In the context of the present invention, the term skin conductance means the galvanic skin response.

A reference statistical analysis step 39 is carried out by comparing averages of physiological recordings originating from different steps of recording values of physiological variables. Such an arrangement allows highlighting the different perceptions between the stimulations and thus grouping together the characterized stimulations.

The method for characterizing an olfactory stimulation also comprises a statistical analysis step, not represented, and carried out between the stimulations. The statistical analysis step is performed by normalizing the variations between before and after the stimulation. The normalization can be carried out of all kinds such as according to the following formula:

$$Vn = \frac{X - Y}{Y}$$

With:
Vn: normalized variation of any one of the physiological variables or any one of its derivatives;
X: a value of any one of the physiological variables or any one of its derivatives after a stimulation; and Y: a value of any one of the physiological variables or any one of its derivatives before a stimulation.

A statistical study is carried out for each of the physiological variables and each of its derivatives in order to compare the different stimulations. The statistical study comprises the use of a statistical method such as the variance analysis as well as the use of a statistical test such as the Student test for example.

The method also comprises a comparing step 40, the comparing step 40 consisting in comparing the first physiological recordings with the second physiological recording, so as to isolate at least one first physiological recording, said at least one first isolated physiological recording being close to the second physiological recording.

Finally, the method comprises a determining step 50, the determining step 50 consisting in determining at least one identified theme, the identified theme being the identified theme associated with the at least one first visual stimulation step 20 which is isolated during the comparing step 40. The determining step 50 is carried out using any method such as an ascending hierarchical classification and/or using a principal component analysis and/or using the dynamic clustering method for example.

According to a preferred embodiment, the method comprises a first step of recording reference measurements 18. Said first step of recording reference measurements 18 is carried out before any one of the stimulation steps and consists in continuously measuring values of physiological variables in order to obtain a first reference recording. The method also comprises a second step of recording reference measurements 19, the second step of recording reference measurements 19 being carried out after or during any one of the stimulation steps and consisting in continuously measuring values of physiological variables in order to obtain a second reference recording. The second step of recording reference measurements 19 is so carried out during a rest sub-step. Such an arrangement allows obtaining a second more reliable reference recording.

Of course, the invention is not limited to the embodiments that are represented and described hereinabove, but covers, on the contrary all variants thereof.

The invention claimed is:

1. A method for characterizing an olfactory stimulation, the method comprising:
   - a plurality of first visual stimulation steps, each first visual stimulation step of the plurality of first visual stimulation steps consisting in carrying out a visual stimulation, the visual stimulation being associated with at least one identified theme;
   - a plurality of first steps of recording values of physiological variables, each first step of recording values of the plurality of first steps of recording values being carried out continuously during a first visual stimulation step among the plurality of first visual stimulation steps, so as to obtain a first physiological recording, the plurality of first steps of recording values of physiological variables thus resulting in obtaining a plurality of first physiological recordings, each first physiological recording of the plurality of first physiological recordings being associated with an identified theme corresponding to the at least one identified theme associated with the first visual stimulation step;
   - a second olfactory stimulation step, the second olfactory stimulation step consisting in carrying out an olfactory stimulation;
   - a second step of recording values of physiological variables, the second step of recording values of physiological variables being carried out continuously during and after the second olfactory stimulation step thus resulting in obtaining a second physiological recording;
   - a comparing step, the comparing step consisting in comparing the plurality of first physiological recordings with the second physiological recording, so as to isolate at least one first physiological recording of the plurality of first physiological recordings, the at least one first physiological recording being close to the second physiological recording; and
   - a determining step, the determining step consisting in determining at least one identified theme, the at least one identified theme being the identified theme associated with the first visual stimulation step which is isolated during the comparing step.

2. The method according to claim 1, comprising a first step of recording reference measurements, the first step of recording reference measurements being carried out before any one of the stimulation steps and consisting in continuously measuring values of physiological variables in order to obtain a first reference recording.

3. The method for according to claim 2, the method comprising a second step of recording reference measurements, the second step of recording reference measurements being carried out after or during any one of the stimulation steps and consisting in continuously measuring values of physiological variables in order to obtain a second reference recording.

4. The method according to claim 3, wherein the plurality of first physiological recordings comprise recordings made using a photoplethysmogram placed on a distal phalanx of a middle finger.

5. The method according to claim 4, wherein the plurality of first physiological recordings comprise recordings made using two electrodermal conductance electrodes on medial phalanxes of index and ring fingers.

6. The method according to claim 5, wherein the plurality of first physiological recordings comprise recordings made using a skin temperature sensor on a distal phalanx of a little finger.

7. The method according to claim 6, wherein the plurality of first physiological recordings comprise recordings of respiratory volumes.

8. The method according to claim 7, wherein the recordings of respiratory volumes comprise a respiratory rhythm as well as inspiration and expiration volumes.

9. The method according to claim 1, wherein the plurality of first physiological recordings comprise recordings made using a photoplethysmogram placed on a distal phalanx of a middle finger.

10. The method according to according to claim 9, wherein a heart rate variability is calculated in frequency and time domain.

11. The method according to claim 1, wherein the plurality of first physiological recordings comprise recordings made using two electrodermal conductance electrodes on medial phalanxes of index and ring fingers.

12. The method according to claim 1, wherein the plurality of first physiological recordings comprise recordings made using a skin temperature sensor on a distal phalanx of a little finger.

13. The method according to claim 1, wherein the plurality of first physiological recordings comprise recordings of respiratory volumes.

14. The method according to claim 13, wherein the recordings of respiratory volumes comprise a respiratory rhythm as well as inspiration and expiration volumes.

15. The method according to claim 13, wherein the recordings of respiratory volumes are made using an abdominal belt allowing measuring of a thoracic or abdominal expansion and contraction and thus generating a respiration wave corresponding to variations of a respiratory volume.

16. The method according to claim 1, wherein each first visual stimulation step of the plurality of first visual stimulation steps comprises a first rest sub-step carried out after the visual stimulation, the first rest sub-step consisting in no longer carrying out stimulation for a first predefined time.

17. The method according to claim 1, wherein the second olfactory stimulation step comprises a second rest sub-step carried out after the olfactory stimulation, the second rest sub-step consisting in no longer carrying out stimulation for a second predefined time.

18. The method according to claim 1, wherein the physiological recordings are divided and filtered.

19. The method according to claim 1, wherein phasic and tonic skin conductances are calculated and represent measurement of electrodermal reaction.

20. The method according to claim 1, wherein a reference statistical analysis step is carried out by comparing averages of physiological recordings originating from different steps of recording values of physiological variables.

* * * * *